US007682606B2

(12) United States Patent
Shastri et al.

(10) Patent No.: US 7,682,606 B2
(45) Date of Patent: Mar. 23, 2010

(54) METHODS OF PRODUCING EDIBLE FUNGI CONTAINING ACTIVATED FOLATES AND NUTRITIONAL SUPPLEMENTS CONTAINING ACTIVATED FOLATES

(75) Inventors: Siddharth Shastri, Los Angeles, CA (US); Peilin Guo, Gardena, CA (US); Jarrow L. Rogovin, Los Angeles, CA (US)

(73) Assignee: Jarrow Formulas, Inc., Los Angeles, CA (US)

( * ) Notice: Subject to any disclaimer, the term of this patent is extended or adjusted under 35 U.S.C. 154(b) by 153 days.

(21) Appl. No.: 12/061,791

(22) Filed: Apr. 3, 2008

(65) Prior Publication Data

US 2008/0292596 A1 Nov. 27, 2008

Related U.S. Application Data

(62) Division of application No. 10/821,609, filed on Apr. 9, 2004, now Pat. No. 7,354,590.

(60) Provisional application No. 60/461,489, filed on Apr. 9, 2003.

(51) Int. Cl.
*A01N 65/00* (2006.01)
*A61K 9/00* (2006.01)
*A61K 47/00* (2006.01)

(52) U.S. Cl. ....................... 424/93.5; 424/400; 424/439

(58) Field of Classification Search ....................... None
See application file for complete search history.

(56) References Cited

U.S. PATENT DOCUMENTS

| | | | |
|---|---|---|---|
| 5,538,523 | A | 7/1996 | Benetti |
| 5,854,404 | A | 12/1998 | Nanba et al. |
| 5,997,915 | A | 12/1999 | Bailey et al. |
| 6,117,462 | A | 9/2000 | Ensley et al. |
| 6,372,462 | B2 | 4/2002 | Wasser et al. |
| 6,383,799 | B1 | 5/2002 | Wasser et al. |
| 6,395,310 | B1 | 5/2002 | Iwasaki |
| 6,451,360 | B2 | 9/2002 | Bailey et al. |
| 6,455,271 | B1 | 9/2002 | Little, II et al. |
| 6,803,226 | B2 | 10/2004 | Suzuki et al. |

FOREIGN PATENT DOCUMENTS

| | | |
|---|---|---|
| JP | 60149379 A | 8/1985 |

OTHER PUBLICATIONS

DW-ACC 2000596789, JP, Aug. 8, 2000, Inoue.
International Search Report of PCT Application No. PCT/US04/10909.
Written Opinion of the International Searching Authority issued on PCT/US04/1909.
"Six Steps to Mushroom Farming", Nov. 2002, pp. 1-8, The Pennsylvania State University, College of Agriculture, Extension Service, University Park, Pennsylvania.
Beetz, Alice & Greer, Lane, "Mushroom Cultivation and Marketing: Horticulture Production Guide", Sep. 1999, pp. 1-18, Appropriate Technology Transfer for Rural Areas (ATTRA), Fayetteville, Arkansas.
Beausejour, Terri Marie, "Getting Started with Mushroom Cultivation: The Wisdom of Simplicity", Mushroom: The Journal of Wild Mushrooming, 1999, pp. 1-16, Moscow, Idaho.

*Primary Examiner*—Christopher R Tate
*Assistant Examiner*—Randall Winston
(74) *Attorney, Agent, or Firm*—McCarter & English LLP

(57) ABSTRACT

Methods are described for producing reduced, methylated, biologically active forms of folate, including 5-methyltetrahydrofolate (i.e. 5-methyltetrahydropteroylglutamic acid), 5-formyltetrahydrofolate, 10-formyltetrahydrofolate and tetrahydrofolate. Edible mushroom-producing fungi are cultivated to enhance the uptake of pteroylmonoglutamate (synthetic folate) into edible portions of the plants. The mushroom-producing fungi reduce and methylate the pteroylmonoglutamates into activated folates. The cultivated mycelia or mushrooms of the mushroom-producing fungi are harvested, and may be consumed directly or processed into oral dosage formats (capsules, tablets, softgels, powders, gel packets, liquids, nutritional bars, beverages) for use as functional foods or nutritional supplements.

4 Claims, 1 Drawing Sheet

METHODS OF PRODUCING EDIBLE FUNGI CONTAINING ACTIVATED FOLATES AND NUTRITIONAL SUPPLEMENTS CONTAINING ACTIVATED FOLATES

This application claims priority to U.S. Provisional Application Ser. No. 60/461,489 filed on Apr. 9, 2003 under 35 U.S.C. §119(e) and is a divisional application under 35 U.S.C. §121 of U.S. patent application Ser. No. 10/821,609 filed Apr. 9, 2004, now U.S. Pat. No. 7,354,590 the contents of which are hereby incorporated by reference.

FIELD OF THE INVENTION

The present invention relates in one aspect to methods of cultivating edible mushroom-producing fungi to enhance the content of reduced, methylated, biologically active folates in the mycelia or mushrooms. In a second aspect, the present invention relates to nutritional supplements comprising edible mycelia or mushrooms which have been cultivated to contain an enhanced content of reduced, methylated biologically active folates. The edible mycelia or mushrooms may be consumed directly, incorporated into foods (i.e. cereals, bars, beverages, etc.) or processed into an oral dosage format.

BACKGROUND OF THE INVENTION

Folic acid is a B vitamin found in many foods. The term folate refers to folic acid and a large family of related compounds. The term folic acid, folate or folacin are the generic terms used for a group of heterocyclic compounds based on the 4-[(pteridin-6-ylmethyl)amino]benzoic acid skeleton conjugated with one or more L-glutamate units. The definition of the term "folic acid" by the IUPAC-IUB Joint Commission on Biochemical Nomenclature (JCBN) states: "The term folates may also be used in the generic sense to designate any members of the family of pteroylglutamates, or mixtures of them, having various levels of reduction of the pteridine ring, one-carbon substitutions and numbers of glutamate residues."

Folates are an important component of the human diet, and several adverse health effects can occur if there is a folate deficiency in the diet. Folates are widely distributed in almost all natural foods, but the highest concentrations are found in yeast, liver, fresh green leafy vegetables, asparagus and lettuce. Moderate sources include beef, veal and wheat. Deficiencies in folic acid levels can result from improper diet, diseases of the upper small intestine (for example, celiac disease or tropical sprue) or increased physical demands (for example, pregnancy, infancy, adolescence or alcoholism).

For people having a folic acid deficiency, biochemical abnormalities may be observed in addition to reductions in blood folic acid and erythrocyte concentrations. The primary role of folic acid is in the metabolism of compounds by transfer of a one carbon group from one compound to another in a process referred to as methylation. Folic acid is required for enzymes that are involved in nucleic acid synthesis and subsequent DNA synthesis. Therefore, deficiency of folic acid may result in neural tube defects, reduced production of pyrimidines, reduced catabolism of serine, tryptophan and histidine, and elevation of homocysteine. Folic acid has a long history of use, in conjunction with vitamin B12, for treatment of macrocytic (or megaloblastic) anemia.

Folic acid deficiencies are generally addressed by enriching foods in folates or by use of dietary supplements containing folates. However, the form of folate used to enrich foods and used in dietary supplements is not the form typically found in foods. The folates found in foodstuffs are typically polyglutamates. Synthetic folates used in dietary supplements and to enrich foods are folic acid or folacin, which contain only one glutamic acid attached to the p-aminobenzoic acid-pteridine ring unit. Therefore, supplements containing synthetic folates may not be effective to meet human metabolic requirements, or to fully correct a folic acid deficiency. Moreover, folic acid supplementation using synthetic folates can mask anemia caused by a vitamin B12 deficiency, which can result in megaloblastic anemia.

While synthetic folates may be processed and used in some people having folate deficiencies, in people who have the 677 TT genotype (that is, in people having a reduced capacity to convert 5, 10-methylene-THF to 5-methyltetrahydrofolate), synthetic folates are not processed for use. Methylated, or activated, folates, such as 5-methyltetrahydrofolate (5-MTHF), circumvent the 677 gene defect, and therefore methylated folates are particularly useful in addressing the folate deficiency and higher homocysteine in persons having this gene variant.

5-MTHF, which is also sometimes referred to as Methyltetrahydropteroylglutamic acid or methylfolate, is one of the most prevalent and important folate in foodstuffs. A form of water soluble B vitamin, 5-MTHF is the predominant form of folate in human circulation. In the folic acid family, 5-MTHF is the reduced and methylated form. As with all forms of folic acid, 5-MTHF has vitamin activity. The vitamin activity is based on the presence of a pterin structure and at least one glutamyl residue linked via peptide bonds to p-aminobenzoic acid. Unlike synthetic folic acid, 5-MTHF does not mask a vitamin B12 deficiency. 5-MTHF requires vitamin B12 to be converted to tetrahydrofolate (THF) in order to enter the cell. In the case of a vitamin B12 deficiency, 5-MTHF would not convert into THF, and therefore it would not enter the cell.

Animal pharmacokinetic data indicates that orally administered 5-MTHF is readily absorbed from the intestinal tract without degradation. Intestinal uptake of 5-MTHF is accomplished by both active, carrier-mediated transport and through passive diffusion. The general characteristics of 5-MTHF in intestinal transport are similar to that of folic acid. In blood serum, 5-MTHF is nonspecifically bound to proteins.

As described above, folic acids are involved in one-carbon metabolism, also known as methylation. 5-MTHF is involved in the synthesis of S-adenosylmethionine (SAM-e). A methyl group from 5-MTHF is donated to homocysteine, which produces the essential amino acid methionine. Methionine is converted by methionine adenosine tranferase (MAT) into SAM-e. The one-carbon transfers are also especially important in purine and pyrimidine synthesis.

Folate-mediated methylation of homocysteine requires the presence of methionine synthetase and vitamin B12 (as a cofactor). The methylation reactions are:

1. 5-MTHF+B12 (cobalamin)→CH3-B12 (methylcobalamin)+tetrahydrofolate

2. CH3-B12 (methylcobalamin)+Homocysteine→B12 (cobalamin)+Methionine

Methylation by folic acid is also important for the de novo biosynthesis of the nucleotides purine and pyrimidine. As a result, folic acid plays an important role in DNA replication and cell division.

To avoid the drawbacks associated with folic acid supplements containing synthetic folates, it would be desirable to develop a supplement containing an enhanced level of natural activated folates in a biologically active form. Accordingly, it is an object of the present invention to overcome one or more drawbacks or disadvantages of the prior art by providing a functional food or a nutritional supplement containing an activated folate that is readily absorbed in the intestines of a human, and which is reduced by natural, non-synthetic processes. Other objects and advantages of the present invention will be apparent to those skilled in the art in view of the detailed description of the invention set forth below.

SUMMARY OF THE INVENTION

The present invention provides a functional food or a nutritional supplement containing high levels of reduced, methylated active folates, particularly 5-MTHF, in an edible mushroom or its mycelia. In one aspect, the invention comprises manipulating the growth environment used to cultivate edible mushroom-producing fungi by adding a synthetic folate to the growth environment. The synthetic folate may be added to the substrate used to grow the mushrooms, or it may be provided in a solution in water supplied to the growing mushrooms. The growing fungi accumulate nutritionally significant amounts of the synthetic folate, which the fungi convert to reduced and methylated folates, such as 5-MTHF. The mycelia or mushrooms produced by the method may be used as a functional food or they may be subject to further processing for incorporation into nutritional supplements.

Among the advantages of the present invention is that it results in nutritional supplements containing reduced, methylated biologically active folates, such as 5-MTHF, in a form that is easily ingested and absorbed in the intestines of a human. A further advantage of the present invention is that it provides a relatively inexpensive and easy to use means for producing a functional food or nutritional supplements having enhanced levels of activated folates. Yet another advantage of the present invention is that it provides a functional food or nutritional supplement containing reduced, methylated, biologically active folates which may be used to correct folic acid deficiencies in individuals having the 677 gene defect.

Other advantages of the present invention will be readily apparent to one skilled in the art based upon the detailed description of preferred embodiments below.

DETAILED DESCRIPTION OF THE PREFERRED EMBODIMENTS

Figure 1:
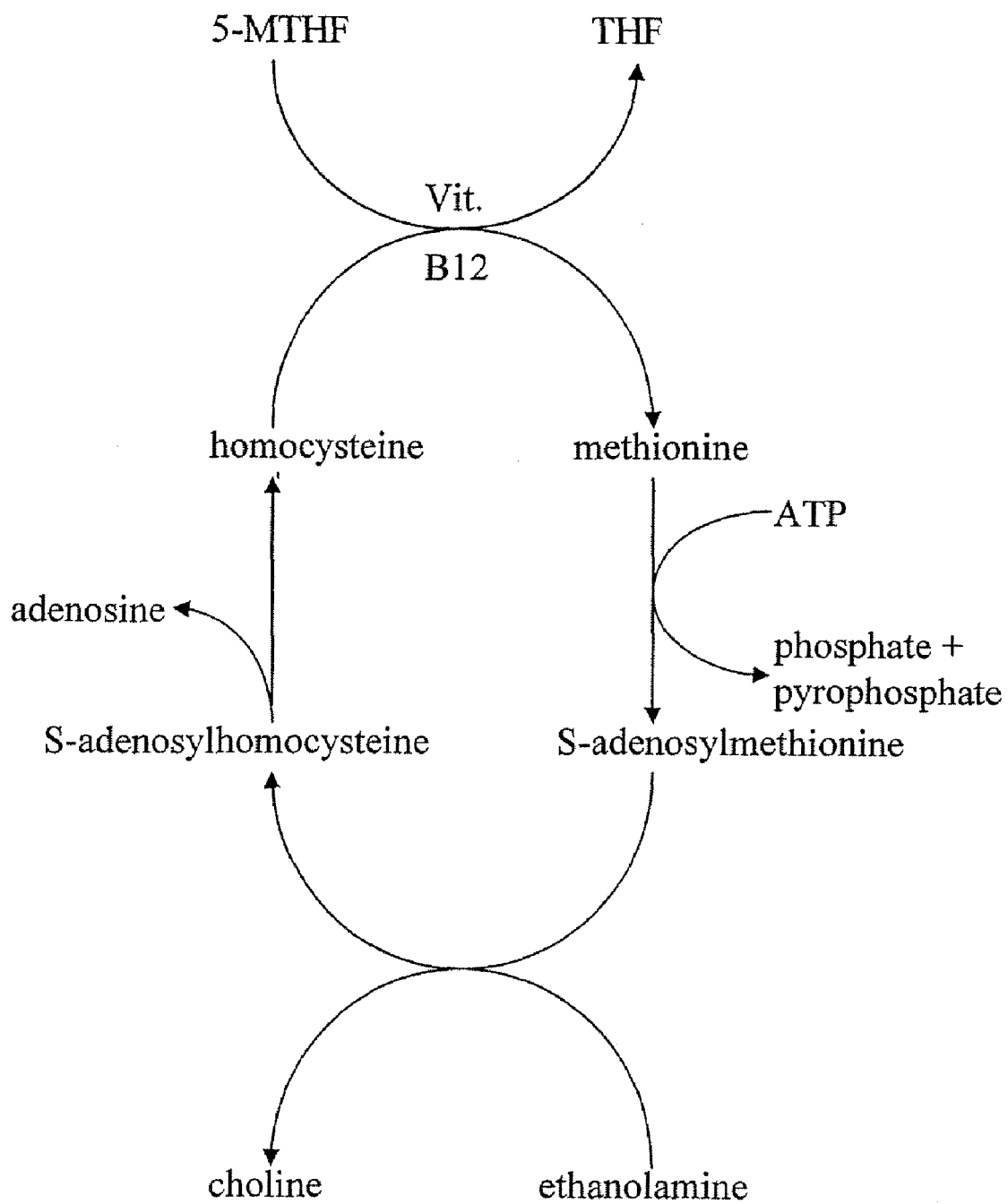
FIG. 1 is a schematic showing the process by which S-adenosylmethionine is synthesized by methylation of homocysteine by 5-MTHF.

The present invention is directed to methods of cultivating edible mushroom-producing fungi to produce mycelia or mushrooms containing a nutritionally significant quantity of reduced, methylated activate folates, and to the functional food or nutritional supplements produced by the methods. Edible mushroom-producing fungi are cultivated in a growth environment, generally comprising a substrate and water, to which synthetic folates have been added. The cultivated fungi grows mycelia and/or mushrooms that take up the synthetic folate and reduce and methylate the synthetic folate to an activated form, such as 5-MTHF. The mycelia or mushrooms can be consumed directly, mixed with other foods and beverages, or they may be further processed and incorporated into nutritional supplements or other foods.

Mushroom-producing fungi are heterotrophic and do not contain chlorophyll. They obtain their nutrients from the environment and from other plant material (the substrate). Cultured mushrooms are typically saprophytes, i.e. organisms that feed on dead plant material. Mushroom spawn are placed on or in a substrate, and the mushroom spawn forms mycelia. Mycelia are filamenous structures that grow throughout the substrate, collecting nutrients by expressing digestive enzymes to break down the substrate materials. When the mycelia mature, specialized hyphae form a solid structure which develops into fruiting bodies. The fruiting body of the fungus is commonly referred to as a mushroom, which is the part of the fungal organism that is typically purchased and consumed.

The method of the present invention comprises the steps of preparing a growth environment for cultivation of edible mushroom-producing fungi, adding a synthetic folate to the growth environment, adding a spawn of the edible mushroom-producing fungi to the growth environment, and cultivating the mushroom-producing fungi in the growth environment for a sufficient time to permit the mycelia or mushrooms to accumulate the synthetic folate and reduce and methylate the synthetic folate to produce a nutritionally significant amount of activated folate in the organism. The organisms naturally process the synthetic folate to produce reduced, methylated folates, such as, for example, 5-MTHF, 5, 10-Methylenetetrahydrofolate, 5, 10-Methenyltetrahydrofolate, and 5-formininofolate. After the fungi have been cultivated in the folate-containing growth environment for a sufficient period of time, the mycelia or mushrooms are harvested, processed and used as a functional food or to produce nutritional supplements. The functional foods or nutritional supplements may be in the form of a processed food, a capsule, a tablet, a soft gel, a powder, a gel packet, a liquid, a bar, or any other form known to those skilled in the art.

The growth environment used for cultivation of the edible mushroom-producing fungi comprises a substrate and any added water, nutrients or other substances that may be used to promote growth of the fungi. The substrate may be any organic material that will support growth of the fungi, such as for example organic brown rice. The synthetic folate may be added to the growth environment by exposing the substrate to a solution containing the synthetic folate and allowing the substrate to absorb synthetic folate from the solution. Alternatively, the synthetic folate may be supplied by adding the synthetic folate to the water in the growth environment. In either case, it is desirable for synthetic folate to be present in the growth environment during the time that the mushroom spawn begins to form mycelia and during subsequent growth of the mycelia and fruiting bodies.

The method of the present invention can be performed using any edible species of mushroom-producing fungi. For example, Maitake (*Grijola frondosa*), shitake (*Lentinola edodes*), or reishi (*Ganodemma luciduni*) can be used. The mushrooms are cultivated using any cultivation method known to those skilled in the art. Methods of mushroom cultivation are provided in, for example, Chang et al., "The Biology and Cultivation of Edible Mushrooms", Academic Press 1978, and Rinaldi et al., "The Complete Book of Mushrooms", Crown Publishers, Inc., 1974, or at www.mushroom.council.com.

Pteroylmonoglutamate, a synthetic folate, is added to the growth medium or substrate used to grow the mushroom-producing fungi. The pteroylmonoglutamate is taken up by the organisms. The fungi process the pteroylmonoglutamates by reducing and methylating the pteroylmonoglutamate into activated folates, such as 5-MTHF, 5-formyltetrahydrofolate, 10-formyltetrahydrofolate and tetrahydrofolate.

The mushroom-producing fungi can be cultivated until the mycelia are at the primordial stage where the fruiting body is about to be formed. The mycelia can be harvested and used to produce functional foods and nutritional supplements as described below. Alternatively, the mycelia can be allowed to fruit and form mushrooms, and the mushrooms can be consumed directly or further processed to produce a functional food or a nutritional supplement.

In one embodiment of the method of the invention, the substrate is prepared by placing organic brown rice soaked in distilled water into one or more containers, such as plastic bottles with filter caps. The rice and plastic bottles are sterilized in a steam autoclave at a temperature of approximately 250-260° F. Sterilization is performed to prevent growth of microbiological organisms that can inhibit or prevent mushroom growth.

A measured amount of acetic acid is added to a volume of distilled water to adjust the pH of the distilled water to between approximately 6-7. The pH adjusted distilled water is heated to a temperature of between approximately 250-260° F. in a steam autoclave to sterilize the water to eliminate microbiological contamination.

Pteroylmonoglutamate is added to the sterilized pH adjusted distilled water to form a pteroylmonoglutamate solution. The pteroylmonoglutamate solution preferably has a concentration of about 400 mg/ml pteroylmonoglutamate. After adding the pteroylmonoglutamate to the distilled water, microbiological tests may be performed on the solution to ensure that the addition of the pteroylmonoglutamate does not result in microbiological contamination of the substrate.

A sufficient volume of the pteroylmonoglutamate solution per gram of brown rice is added to the plastic bottles to ensure that the edible fungi will accumulate and process the desired quantity of the synthetic folate. Preferably, the volume of the pteroylmonoglutamate solution per gram of brown rice is between about 0.5 ml pteroylmonoglutamate solution per gram of brown rice to about 10 ml pteroylmonoglutamate solution per gram of brown rice. A spawn of mushroom-producing fungi is then introduced to each of the plastic bottles, and the bottles are placed in an environmentally controlled room for germination. The temperature and humidity are maintained within ranges known to those skilled in the art for growth of the type of mushroom spawn used.

The bottles are monitored daily to observe the progress of mycelial growth in the plastic bottles. In this embodiment, when the mycelia have grown to the point where they are about to form fruiting bodies (i.e. the mycelia has reached the primordial stage), the plastic bottles are emptied into trays with stainless steel wire mesh for drying. The material from the bottles is dried using air heated to no greater than 120° F.

The dried material is milled to a 60-mesh size. The powdered material is placed in plastic bags (approximately 15 kg each), and the plastic bags are placed in 5 gallon buckets with air-tight lids. The dried material may be tested for microbiological growth prior to packaging.

Mycelia from mushroom-producing fungi cultivated by the method described above were analyzed to determine the level of 5-MTHF (one of a group of activated folates) contained in the mushrooms. As shown in Table I below, the mycelia contained elevated levels of 5-MTHF as compared to mycelia grown without addition of a synthetic folate to the growth environment. These results demonstrate that mushroom-producing fungi grown with synthetic folate added to the growth environment will take up the synthetic folate and reduce and methylate the synthetic folate into 5-MTHF and other activated folates.

TABLE 1

Comparison of 5-MTHF Content in Mycelia Grown With and Without Addition of Synthetic Folic Acid to Growth Environment

| | Level of 5-MTHF/g Mycelia Powder |
|---|---|
| Synthetic Folic Acid Added | 65.9 mg/g |
| No Synthetic Folic Acid Added | 4.77 mg/g |

In another embodiment of the method of the invention, para-aminobenzoic acid (PABA) can be added to the growth environment with the pteroylmonoglutamate. PABA serves as a substrate for synthesis of folates, and addition of PABA to the substrate can further enhance the processing of the synthetic folate by the mushroom-producing fungi, thereby increasing the level of reduced, methylated active folates in the mycelia or mushrooms.

The edible mushroom-producing fungi cultivated by the methods of the present invention can be used to provide reduced, methylated active folates to those having a folate deficiency. A preferred use of the edible mushroom-producing fungi grown by the methods described above is in the treatment of cardiovascular disease in individuals with hypothyroidism. Hypothyroidism is observed to cause elevated homocysteine, which may be an independent risk factor for cardiovascular disease. The pathophysiology of cardiovascular disease caused by hypothyroidism is thought to be homocysteine-induced atherosclerosis. Elevated homocysteine is caused by a suppression of methylenetetrahydrofolate reductase, which is responsible for converting 5,10-methylenetetrahydrofolate to 5-methyltetrahydrofolate. Reduce amounts of 5MTHF results in fewer transfers of methyl groups to vitamin B12 for eventual methylation of homocysteine. A supplement containing reduced, methylated, active folate, such as the supplement of the present invention, bypasses the suppression of methylenetetrahydrofolate reductase and can be used to counter cardiovascular dysfunction in hypothyroidism. This can be accomplished by administering to an individual having hypothyroidism a supplement having a therapeutically effective amount of reduced, methylated active folate, such as those described herein.

While the methods set forth herein are not intended to be limited to any particular mechanism of action, it appears that the nutritional supplements produced by the methods set forth herein contain an enhanced amount of the L-isomer of 5-MTHF. Studies have indicated that the L-isomer of 5-MTHF is superior to racemic mixtures containing equal amounts of the L-isomer and the D-isomer when administered to a human for the purpose of reducing homocysteine. Because the D-isomer of 5-MTHF may compete with the L-isomer for biological absorption and cellular uptake, a nutritional supplement containing an enhanced level of the L-isomer of 5-MTHF is desirable for use to increase folate levels in humans. In the methods of the present invention, the mushrooms may produce enhanced levels of the naturally active L-isomer of 5-MTHF, which is superior to synthetic folates containing racemic D,L isomer combination of activated folates. Preferably, the methods of the present invention will result in nutritional supplements containing the chirally pure L-isomer of 5-MTHF.

The mushrooms or mycelia containing enhanced levels of activated folates can be processed for use in functional foods and nutritional supplements. The mushrooms or mycelia may be processed and included in capsules, tablets, softgels, nutritional powders, drinks or beverages, soft chews or nutritional bars. The mushrooms or mycelia may be combined with liposomes or in emulsions, and may comprise suitable solid or gel phase carriers or excipients. Examples of carriers or excipients include, but are not limited to, calcium carbonate, calcium phosphate, various sugars, starches, cellulose derivatives, gelatin and polymers such as polyethylene glycols. Alternatively, the mushrooms or mycelia may be ground into a powder and added directly to foods such as cereals, soups, salads or sandwiches.

When provided in an oral dosage format, the capsules, tablets or softgel will preferably provide a dosage of between about 10 μg and about 5000 μg of activated folates per capsule, tablet or softgel, and more preferably between about 200 μg and 2000 μg of activated folates per capsule, tablet or softgel.

It will be apparent to those skilled in the art that modifications can be made to the methods described herein without departing from the scope or spirit of the present invention. For example, different substrates may be used for mushroom cultivation, the substrate may be placed in any appropriate type of container different containers may be used, or any other appropriate modifications to the cultivation method known to those skilled in the art may be made. Accordingly, the preferred embodiments described herein should be taken in an illustrative, rather than a limiting, sense.

We claim:

1. A nutritional supplement containing reduced, methylated active folates comprising edible mushroom-producing fungi grown by supplying a growth environment for cultivation of edible mushroom-producing fungi wherein the growth environment comprises a substrate and water; adding a synthetic folate to the growth environment; combining a spawn of at least one edible mushroom-producing fungi selected from the group consisting of *Lentinola edodes, Ganoderma lucidum* and *Grifola Frondosa* with the substrate; and cultivating the edible mushroom-producing fungi in the growth environment for a sufficient time to permit the mushroom-producing fungi to accumulate a nutritionally significant amount of methylated folate, wherein the nutritional supplement comprises between about 200 μg and about 2000 μg of reduced, methylated active folates.

2. The nutritional supplement of claim 1, wherein the reduced, methylated active folates comprise the L-isomer of 5-methyltetrahydrofolate (5-MTHF).

3. The nutritional supplement of claim 1, wherein the edible mushrooms are processed and incorporated in a capsule, tablet, soft gel powder or gel packet.

4. A method for treating cardiovascular disease in humans having hypothyroidism comprising the step of administering a therapeutically effective amount of the nutritional supplement of claim 1.

* * * * *